(12) United States Patent
Murphy

(10) Patent No.: US 9,692,557 B2
(45) Date of Patent: Jun. 27, 2017

(54) APPARATUS AND METHODS FOR ADMINISTERING TREATMENT WITHIN A BODILY DUCT OF A PATIENT

(71) Applicants: Stryker European Holdings I, LLC, Kalamazoo, MI (US); Stryker Corporation, a Michigan Corporation, Kalamazoo, MI (US)

(72) Inventor: Murtagh M. Murphy, Cork (IE)

(*) Notice: Subject to any disclaimer, the term of this patent is extended or adjusted under 35 U.S.C. 154(b) by 0 days.

(21) Appl. No.: 14/991,032

(22) Filed: Jan. 8, 2016

(65) Prior Publication Data

US 2016/0220793 A1    Aug. 4, 2016

Related U.S. Application Data

(60) Provisional application No. 62/112,135, filed on Feb. 4, 2015.

(51) Int. Cl.
  *A61M 25/10* (2013.01)
  *A61M 25/00* (2006.01)
  (Continued)

(52) U.S. Cl.
  CPC .......... *H04L 1/0057* (2013.01); *A61M 25/007* (2013.01); *A61M 25/0108* (2013.01);
  (Continued)

(58) Field of Classification Search
  CPC ............ A61M 25/007; A61M 25/1018; A61M 25/10185; A61M 2025/1052;
  (Continued)

(56) References Cited

U.S. PATENT DOCUMENTS 4,968,306 A  *  11/1990  Huss .................... A61M 25/007
                                                      604/264
5,776,100 A  *  7/1998  Forman ................. A61M 25/09
                                                      604/102.03
(Continued)

FOREIGN PATENT DOCUMENTS

WO       2011094476 A1     8/2011

OTHER PUBLICATIONS

International Search Report mailed Mar. 18, 2016 in corresponding International Application No. PCT/US16/12584.

*Primary Examiner* — Nathan R Price
*Assistant Examiner* — Weng Lee
(74) *Attorney, Agent, or Firm* — Edell, Shapiro & Finnan LLC

(57) ABSTRACT

Apparatus and methods for administering treatment within a bodily duct of a patient. According to one implementation a treatment catheter having an expandable structure disposed at an end thereof is provided that includes an elongate hollow shaft having a one or more first through holes and one or more second through holes spaced axial apart, the one or more first through holes residing beneath the expandable structure. A sleeve positioned along an outer surface of the hollow shaft is moveable between first and second axial positions to respectively permit or inhibit the flow of a treatment agent through the one or more second through holes into the bodily duct. An elongate wire having a seal unit is positioned within an inner lumen of the hollow shaft. The seal unit is moveable between first and second axial positions to respectively permit or inhibit the flow of an inflation medium between a cavity of the expandable structure and the inner lumen of the hollow shaft through the one or more first through holes.

27 Claims, 29 Drawing Sheets

(51) Int. Cl.
*H04L 1/00* (2006.01)
*H04L 12/18* (2006.01)
*H04L 5/00* (2006.01)
*H04W 4/06* (2009.01)
*H03M 13/11* (2006.01)
*H03M 13/25* (2006.01)
*H03M 13/27* (2006.01)
*H03M 13/29* (2006.01)
*H03M 13/00* (2006.01)
*A61M 25/01* (2006.01)
*H03M 13/15* (2006.01)
*H03M 13/09* (2006.01)
*A61M 5/00* (2006.01)

(52) U.S. Cl.
CPC .. *A61M 25/10185* (2013.11); *H03M 13/1165* (2013.01); *H03M 13/255* (2013.01); *H03M 13/271* (2013.01); *H03M 13/2778* (2013.01); *H03M 13/2906* (2013.01); *H03M 13/6356* (2013.01); *H03M 13/6362* (2013.01); *H04L 1/0041* (2013.01); *H04L 1/0071* (2013.01); *H04L 5/0053* (2013.01); *H04L 12/18* (2013.01); *H04L 12/1886* (2013.01); *H04W 4/06* (2013.01); *A61M 5/007* (2013.01); *A61M 2025/105* (2013.01); *A61M 2025/1052* (2013.01); *A61M 2025/1081* (2013.01); *H03M 13/09* (2013.01); *H03M 13/152* (2013.01); *H04L 2001/0093* (2013.01)

(58) Field of Classification Search
CPC .. A61M 2025/1063; A61M 2025/1081; A61M 2025/105; A61M 2025/0079; A61M 2025/0175; A61M 2025/0186; A61M 2025/0018; A61M 25/003; A61M 25/10184
See application file for complete search history.

(56) References Cited

U.S. PATENT DOCUMENTS

| | | | |
|---|---|---|---|
| 5,779,731 A | 7/1998 | Leavitt | |
| 5,807,328 A * | 9/1998 | Briscoe | A61M 25/0075 604/102.02 |
| 6,231,588 B1 * | 5/2001 | Zadno-Azizi | A61B 17/12022 604/99.02 |
| 6,755,813 B2 * | 6/2004 | Ouriel | A61B 17/22 604/264 |
| 7,041,080 B2 * | 5/2006 | Dion | A61M 25/1018 604/97.01 |
| 7,713,282 B2 | 5/2010 | Frazier et al. | |
| 7,959,584 B2 * | 6/2011 | Esksuri | A61F 2/013 600/585 |
| 8,197,441 B2 * | 6/2012 | Webler | A61F 2/013 604/103.01 |
| 8,715,228 B2 | 5/2014 | Barki | |
| 8,945,160 B2 * | 2/2015 | Krolik | A61B 17/22032 604/509 |
| 2002/0026211 A1 * | 2/2002 | Khosravi | A61F 2/01 606/200 |
| 2005/0102020 A1 | 5/2005 | Grayzel et al. | |
| 2006/0264897 A1 * | 11/2006 | Lobl | A61M 39/0208 604/506 |
| 2007/0083253 A1 | 4/2007 | Fischell et al. | |
| 2007/0088257 A1 * | 4/2007 | Fisher | A61M 25/10 604/103.04 |
| 2011/0071497 A1 | 3/2011 | Alinsod et al. | |
| 2013/0184644 A1 | 7/2013 | Vo et al. | |
| 2013/0292365 A1 * | 11/2013 | Cornish | A61M 25/09 219/121.72 |
| 2014/0371709 A1 * | 12/2014 | Allen | A61M 25/10 604/503 |

* cited by examiner

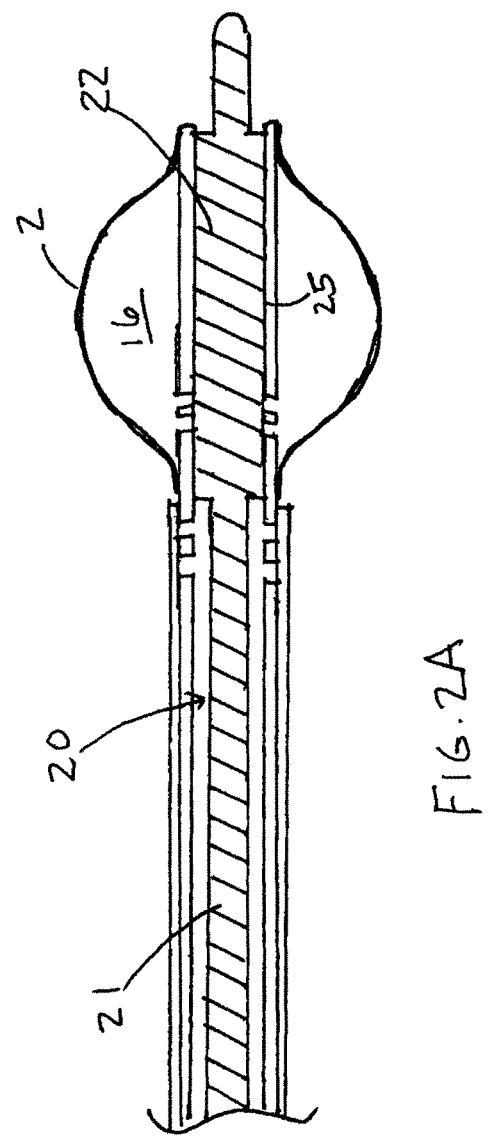

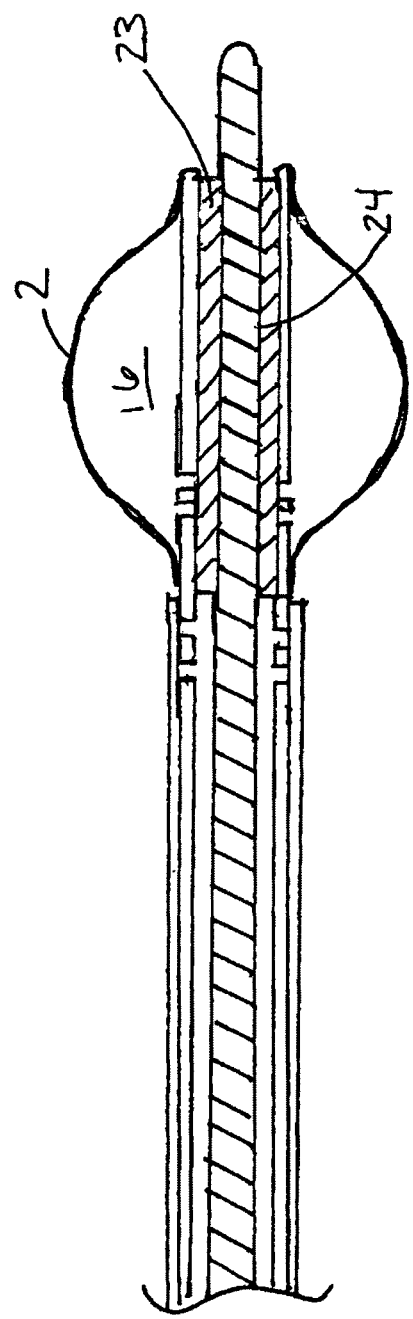

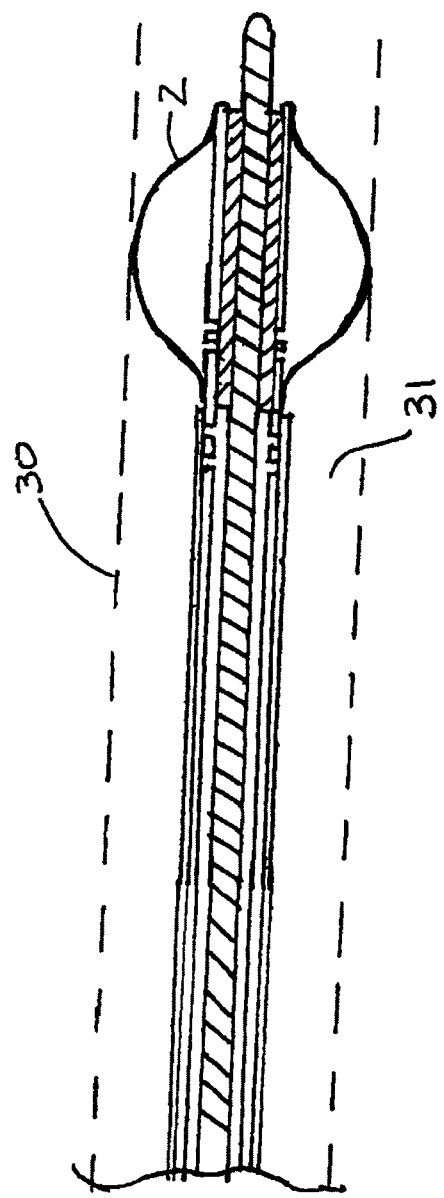

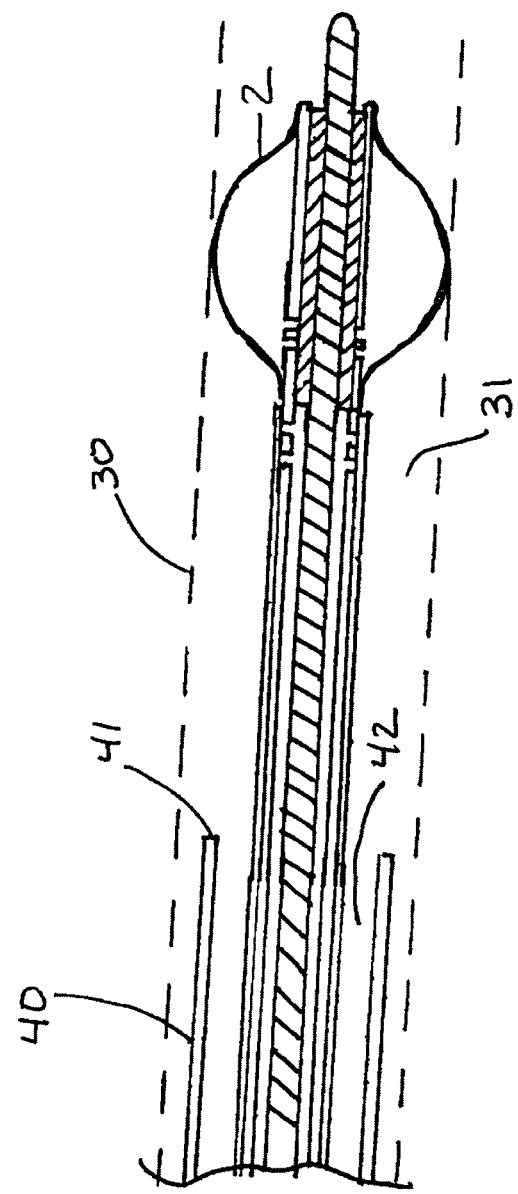

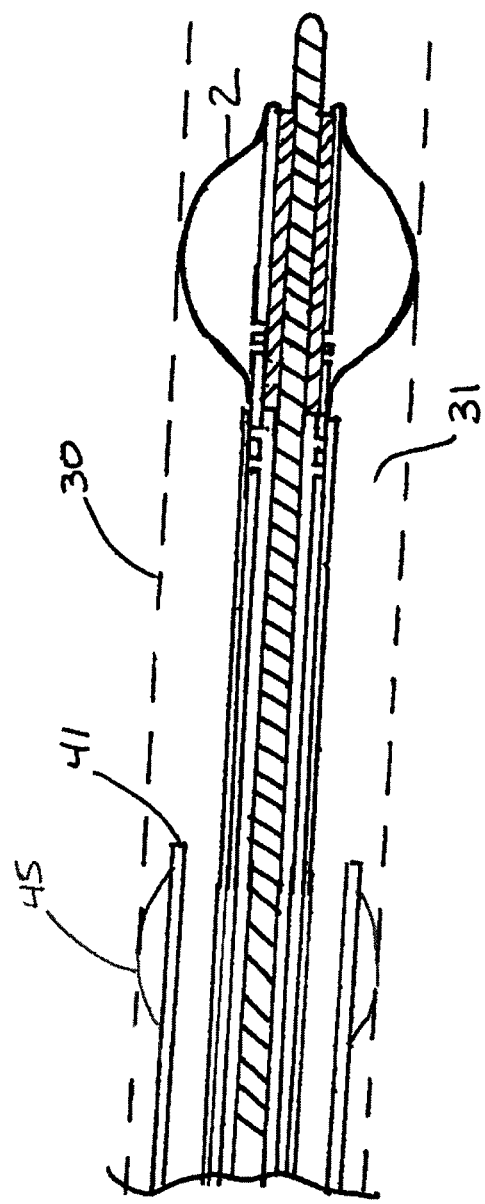

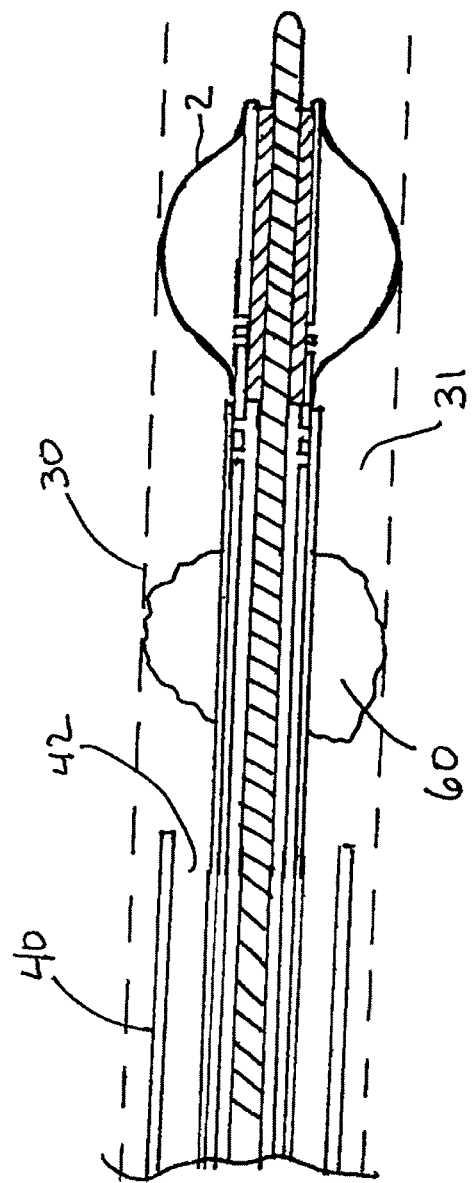

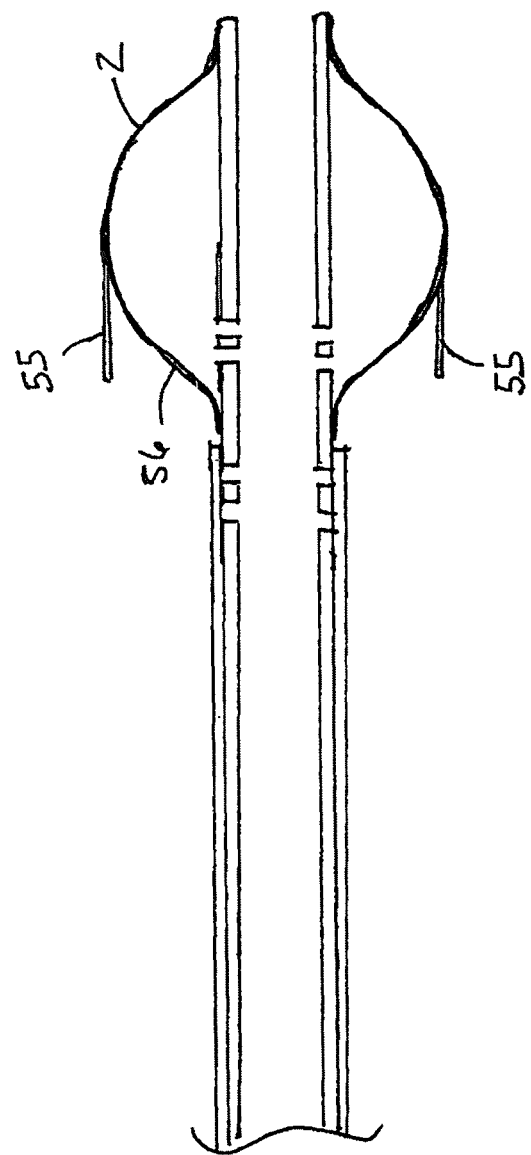

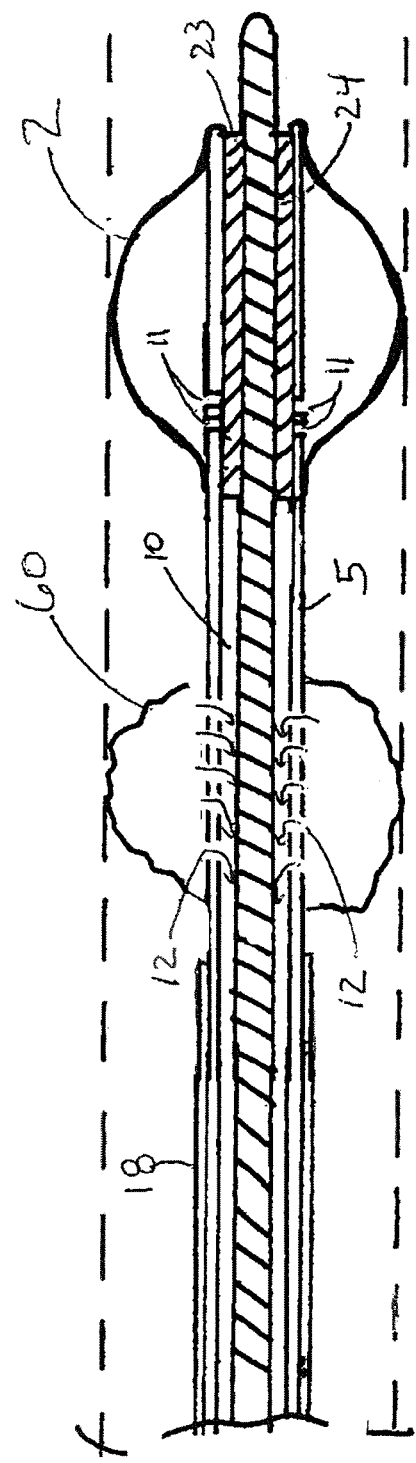

APPARATUS AND METHODS FOR ADMINISTERING TREATMENT WITHIN A BODILY DUCT OF A PATIENT

CROSS-REFERENCE TO RELATED APPLICATIONS

This application claims the benefit and priority to U.S. Provisional Application No. 62/112,134, filed Feb. 4, 2015.

TECHNICAL FIELD

This application relates to apparatus and methods for administering treatment within the vasculature or other internal bodily ducts of a patient.

SUMMARY OF THE DISCLOSURE

According to some implementations a treatment catheter for placement in a bodily duct of a patient is provided that comprises: an expandable structure disposed at an end thereof; an elongate hollow shaft having a one or more first through holes and one or more second through holes spaced axial apart, the one or more first through holes residing beneath the expandable structure; a sleeve positioned along an outer surface of the elongate hollow shaft moveable between first and second axial positions to respectively permit or inhibit the flow of a treatment agent through the one or more second through holes into the bodily duct; and an elongate wire having a seal unit positioned within an inner lumen of the elongate hollow shaft, the seal unit moveable between first and second axial positions to respectively permit or inhibit the flow of an inflation medium between a cavity of the expandable structure and the inner lumen of the hollow shaft through the one or more first through holes.

According to some implementations a treatment catheter for placement in a bodily duct of a patient is provided that comprises: an expandable structure capable of assuming an expanded configuration and an unexpanded configuration, the expandable structure comprising a proximal end portion and a distal end portion, at least the distal end portion of the expandable structure being adapted to occlude the passage of a fluid there through when the expandable structure assumes the expanded configuration, the expandable structure having a proximal end and a distal end; an elongate hollow shaft having a proximal end portion and a distal end portion, the proximal and distal ends of the expandable structure being coupled to the distal end portion of the hollow shaft at first and second longitudinal locations, respectively, the second longitudinal location being distal to the first longitudinal location, a wall of the hollow shaft has an inner surface and an outer surface, the inner surface of the wall defining an inner lumen that extends between a location at or near a proximal end of the hollow shaft to a position inside the expandable structure, the hollow shaft having one or more first holes and one or more second holes that extend through the wall, the one or more first holes being located proximal to the first longitudinal location, the one or more second holes being located inside the expandable structure between the first and second longitudinal locations; an elongate wire located in the inner lumen of the hollow shaft and movable axially within the inner lumen between at least a first axial position and a second axial position, a distal end portion of the elongate wire comprising a seal unit configured to occlude the one or more second holes in the wall of the hollow shaft when the elongate wire is in the first axial position, when the elongate wire is in the second axial the seal unit is positioned away from the one or more second through holes so that the inner lumen of the hollow shaft is in fluid communication with an inner cavity of the expandable structure; and a sleeve slideable along the outer surface of the hollow shaft between at least a third axial position and a fourth axial position, when in the third axial position a distal portion of the sleeve is positioned over the one or more first through holes in the wall of the hollow shaft to occlude flow through the one or more first through holes, when in the fourth axial position the sleeve is positioned proximal to the one or more first through openings so that the inner lumen is in fluid communication with an exterior of the hollow shaft.

According to some implementations a method of administering a treatment agent to a treatment site in a bodily duct of a patient using one of the aforementioned treatment catheters is provided, the method comprising: positioning the treatment catheter in the bodily duct so that the entirety of the expandable structure resides distal to the treatment site; placing the elongate wire in the second axial position; introducing an inflation medium into a proximal end of the inner lumen of the hollow shaft at a pressure sufficient to cause the inflation medium to flow though the first one or more holes to cause the expandable structure to assume the expanded configuration, with the expandable structure being in the expanded configuration moving the sleeve from the third axial position to the fourth axial position; and introducing the treatment agent into the proximal end of the inner lumen of the hollow shaft at a pressure sufficient to cause the treatment agent to flow through the second one or more holes and into the bodily duct.

According to some implementations a method of administering a treatment agent to a treatment site in a bodily duct of a patient using one of the aforementioned treatment catheters is provided, the method comprising: positioning the treatment catheter in the bodily duct so that the entirety of the expandable structure resides distal to the treatment site; placing the elongate wire in the second axial position; introducing an inflation medium into a proximal end of the inner lumen of the hollow shaft at a pressure sufficient to cause the inflation medium to flow though the first one or more holes to cause the expandable structure to assume the expanded configuration, moving the elongate wire from the second axial position to the first axial position; with the elongate wire in the second axial position and the expandable structure being in the expanded configuration moving the sleeve from the third axial position to the fourth axial position; and introducing the treatment agent into the proximal end of the inner lumen of the hollow shaft at a pressure sufficient to cause the treatment agent to flow through the second one or more holes and into the bodily duct.

According to some implementations a method for removing an obstruction in a bodily duct of a patient using one of the aforementioned treatment catheter is provided, the method comprising: obtaining an intermediate treatment catheter that includes an elongate lumen that is open at a distal end thereof; advancing the intermediate catheter into the bodily duct of the patient so that the open distal end of the elongate lumen is positioned near and proximal to the obstruction; advancing the treatment catheter through the elongate lumen of the intermediate catheter and into the bodily duct so that the entirety of the expandable structure resides distal to the obstruction; placing the elongate wire in the second axial position; introducing an inflation medium into a proximal end of the inner lumen of the hollow shaft at a pressure sufficient to cause the inflation medium to flow though the first one or more holes to cause the expandable structure to assume the expanded configuration; with the expandable structure being in the expanded configuration moving the sleeve from the third axial position to the fourth axial position; introducing a treatment agent into the proximal end of the inner lumen of the hollow shaft at a pressure sufficient to cause the treatment agent to flow through the second one or more holes and into the bodily duct; and aspirating at least a portion of the treatment agent through the elongate lumen of the intermediate catheter.

According to some implementations a balloon catheter adapted for removing an obstruction within a duct of a patient is provided that comprises: an elongate catheter having a proximal end, a distal end and an inner lumen; and a balloon attached to an outer surface of the elongate catheter, the balloon having an inner cavity that is in fluid communication with the inner lumen of the elongate catheter, the balloon inflatable from an unexpanded state to an expanded state and having attached to an outer surface thereof a plurality proximally extending members configured to pierce the obstruction.

These and other advantages and features will become evident in view of the drawings and the detailed description.

BRIEF DESCRIPTION OF THE DRAWINGS

FIGS. 2A and 2B show a cross-section view of the treatment catheter of FIG. 1 having an elongate wire with an integral seal unit disposed therein.

FIGS. 3A and 3B illustrate other implementations wherein the seal unit is attached to an outer surface of the elongate wire.

FIGS. 6A and 6B illustrate a manner of locally administering treatment at a location within a bodily duct of a patient.

FIGS. 7A-D illustrate treatment systems the include a treatment catheter and an intermediate catheter.

FIG. 8A illustrates a placement of a treatment catheter in a bodily duct with the treatment agent infusion ports and expandable structure being located distal to an obstruction.

FIG. 9 illustrates another implementation with a proximal end portion of the expandable structure comprising a porous structure or one or more holes extending there through.

FIGS. 13A-C illustrate a catheter having an expandable structure with proximally extending members, according to some implementations.

FIGS. 15A and 15B illustrate an assembly for removing an obstruction from the duct of a patient according to another implementation.

DETAILED DESCRIPTION

Figure 1:
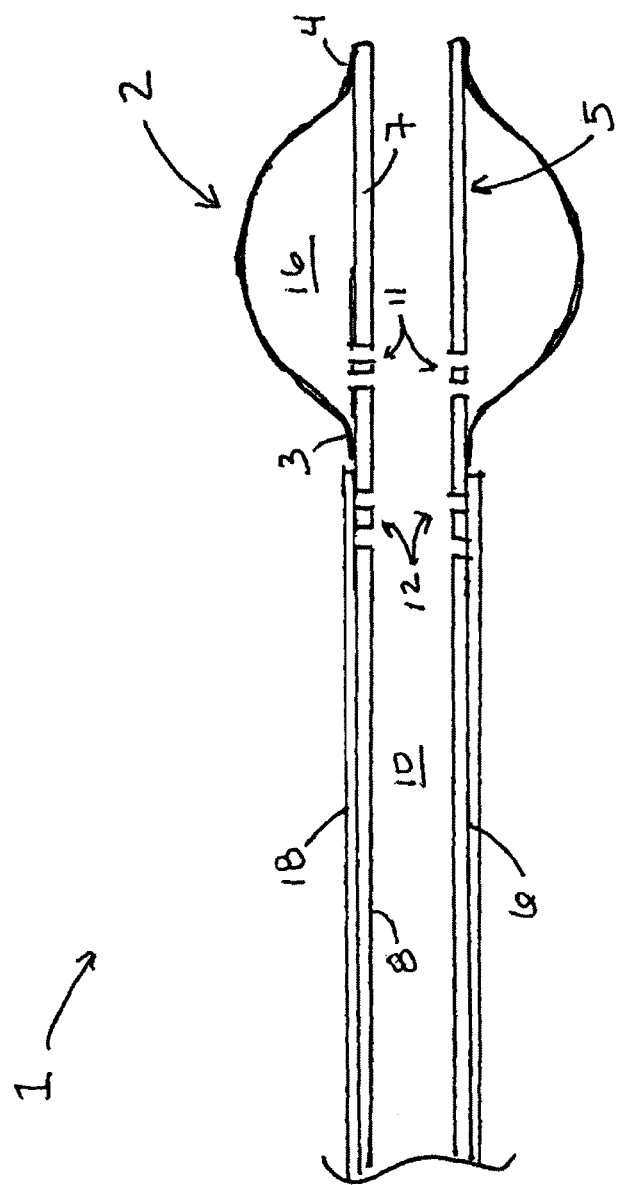
FIG. 1 is a cross-section view of a treatment catheter according to one implementation.

FIG. 1 shows a cross-section view of a treatment catheter 1 according to one implementation. The treatment catheter 1 includes an expandable structure 2 having a proximal end 3 and a distal end 4. Each of the proximal end 3 and distal end 4 of the expandable structure 2 is coupled to a distal portion of an elongate hollow shaft 5 that extends along a substantial length of the treatment catheter 1. The expandable structure 2 is capable of assuming an expanded state (as shown in the figures) and an unexpanded state wherein the inner wall of the expandable structure 2 rests against an outer surface 6 of the wall 7 of the elongate outer shaft 5. The expandable structure 2 is typically maintained in the unexpanded state when being delivered or withdrawn through the bodily duct. According to some implementations the expandable structure 2 is an inflatable balloon as depicted in the figures. According to other implementations the expandable structure 2 comprises a covered expandable and collapsible cage having an inner cavity that is capable of being infused with an inflation medium to effectuate an expansion of the expandable structure. According to some implementations, in use, the inflation medium comprises a contrast medium that permits a visualization of the inflation and/or movement of the expandable structure 2 when it is deployed within the anatomy of a patient. The balloon and cover may comprise any of a variety of known materials that are capable of fully or at least partially containing the inflation medium within the expandable structure 2 so as to maintain the expandable structure in an expanded state. According to some implementations the expandable structure 2 has a length of between 2.0 and 10.0 millimeters, and preferably between 2.0 and 5.0 millimeters.

The elongate hollow shaft 5 includes an inner lumen 10 that is defined by an inner surface 8 of the wall 7. According to some implementations the elongate hollow shaft 5 possesses one or more first through openings 11 located in the wall 7 beneath the expandable structure 2, the one or more first through openings 11 permitting the inner lumen 10 of the elongate hollow shaft 5 to be in fluid communication with an interior cavity 16 of the expandable structure 2. The elongate hollow shaft 5 further includes one or more second through openings 12 located proximal to the expandable structure 2. Overlying the one or more second through openings 12 is a sleeve 18 that is slideable along the outer surface 6 of the elongate hollow shaft 5 between a first axial position as depicted in FIGS. 1-4, 6A, 7A, 8A and 9 and a second axial position as depicted in FIGS. 5, 6B, 7B and 8B. According to some implementations a compression fit exists between the inner surface of the sleeve 18 and the outer surface 6 of the elongate hollow shaft 5. As shown in FIGS. 4, 6A, 7A and 8A, when the sleeve 18 is in the first axial position it lies over the one or more second through openings 12 to inhibit fluid communication between the inner lumen 10 of the elongate hollow shaft 5 and the lumen 31 of the bodily duct 30. As shown in FIGS. 5, 6b, 7B and 8B, when the sleeve 18 is in the second axial position it does not lie over the one or more second through openings 12 to permit fluid communication between the inner lumen 10 of the elongate hollow shaft 5 and the lumen 31 of the bodily duct 30.

Figure 4:
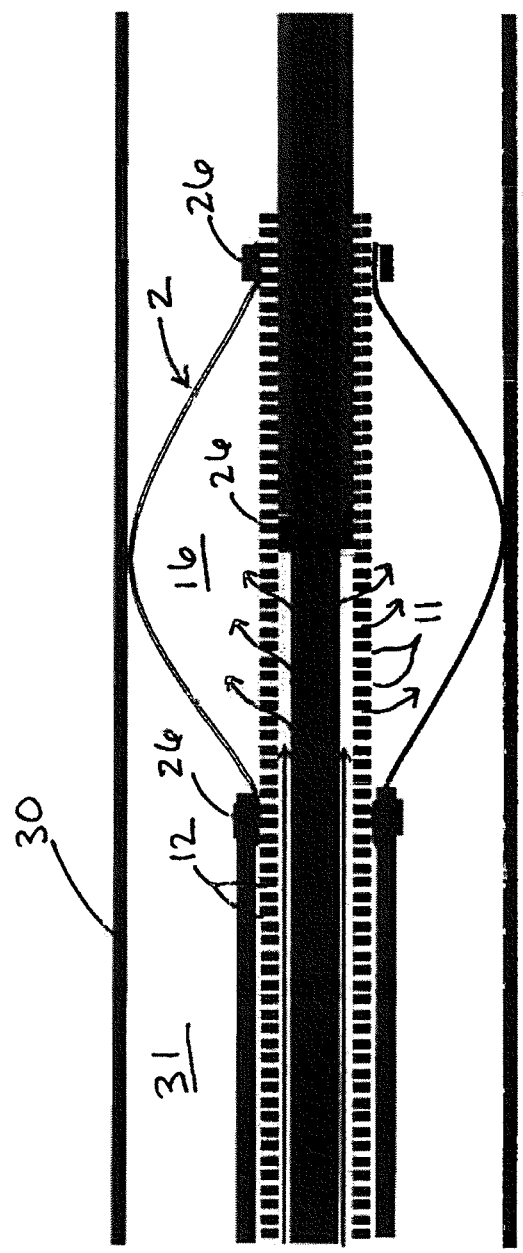
FIG. 4 shows a treatment catheter with a seal unit positioned to permit a flow of an inflation medium into the expandable structure of the treatment catheter.
Figure 5:
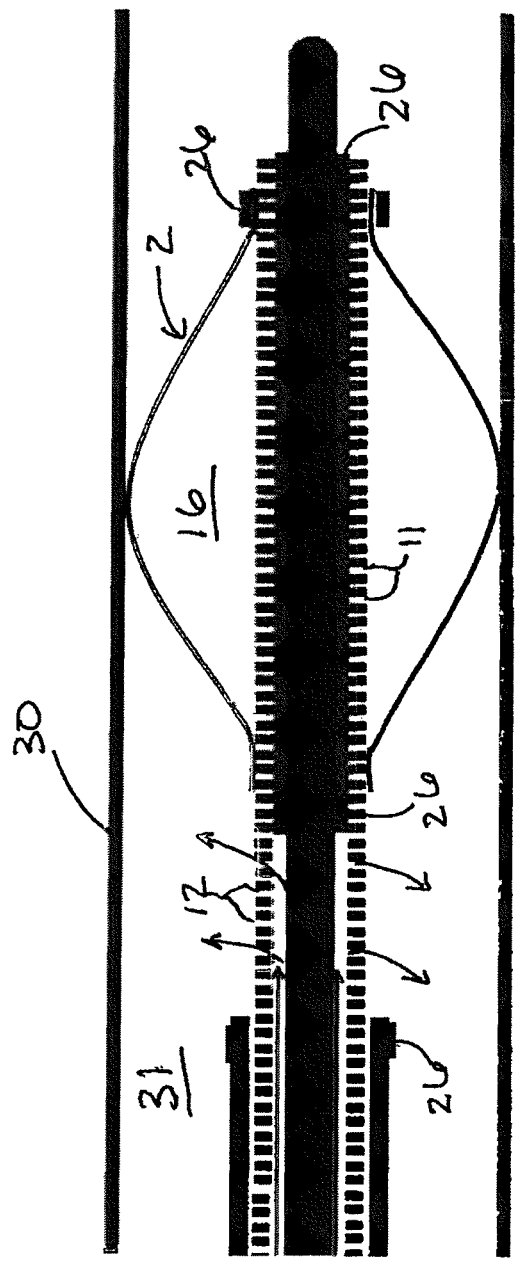
FIG. 5 shows a treatment catheter with the seal unit positioned to occlude the flow into inflatable structure and the sleeve positioned to permit the flow of a treatment agent into the bodily duct of a patient.
Figure 10:
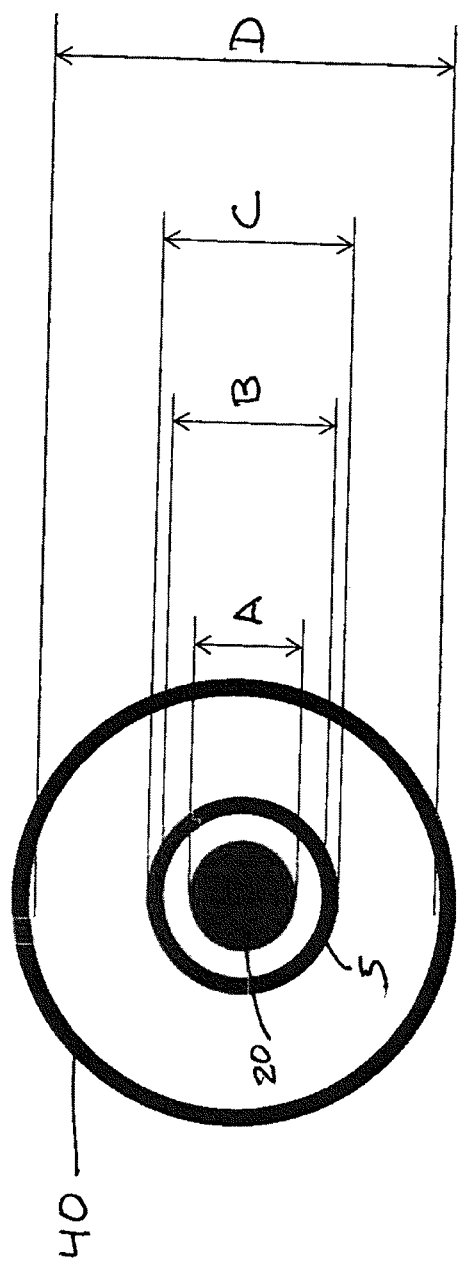
FIG. 10 illustrates the diametric relationship among the various parts of a treatment catheter according to some implementations.

According to some implementations the elongate hollow shaft 5 comprises a thin-walled and flexible structure that enables the treatment catheter 1 to be delivered through the tortuous anatomy of the patient, such as through the vascular system of a patient. According to some implementations, as shown in FIGS. 1-4 and 6-8, the one or more first and second through openings 11 and 12 are formed in the wall 7 of the elongate hollow shaft at discrete locations. According to other implementations the one or more first and second through openings 11 and 12 comprise a subset of a larger number of through openings that extend along a major length of the elongate hollow shaft 5 as exemplified in FIGS. 4 and 5. The elongate hollow shaft 5 may comprise a polymer, metal, composite or any other material suitable for delivering an inflation medium (e.g. saline solution) or treatment medium (e.g. drug) through the inner lumen 10 while endowing the treatment catheter 1 with the requisite flexibility and pushability for being delivered to the treatment site. According to some implementations the elongate hollow shaft 5 is made of a metal, such as a metal hypotube. The use of a metal construct allows the wall 7 of the elongate hollow shaft 5 to have a thinner thickness profile than is otherwise achievable using a polymer construct. This is advantageous in situations where it is important to maintain the overall diameter of the treatment catheter 1 to a minimum, such as when being used to treat a site located within the neurovascular system of a patient. According to some implementations the hypotube is cut using a blade (e.g. rotating disk) or a laser to form the one or more first and second through openings 11 and 12. In the implementations of FIGS. 4 and 5 a majority of the length of the hypotube may be cut in a manner to form a repeating double helix backbone that allows the elongate hollow shaft 5 to be flexible in all directions. According to one such implementation the proximal end portion of the hypotube comprises a solid or substantially solid wall to assist in pushability with the number of cuts per length increasing along the length of the wall 7 so that the flexibility of the elongate hollow shaft 5 incrementally increases along its length in the distal direction. According to one implementation the elongate hollow shaft 5 is made of nitinol and has an outer diameter C (see FIG. 10) of between about 0.025 and 0.035 inches and a wall thickness of between about 0.0015 to 0.003 inches.

Figure 2B:
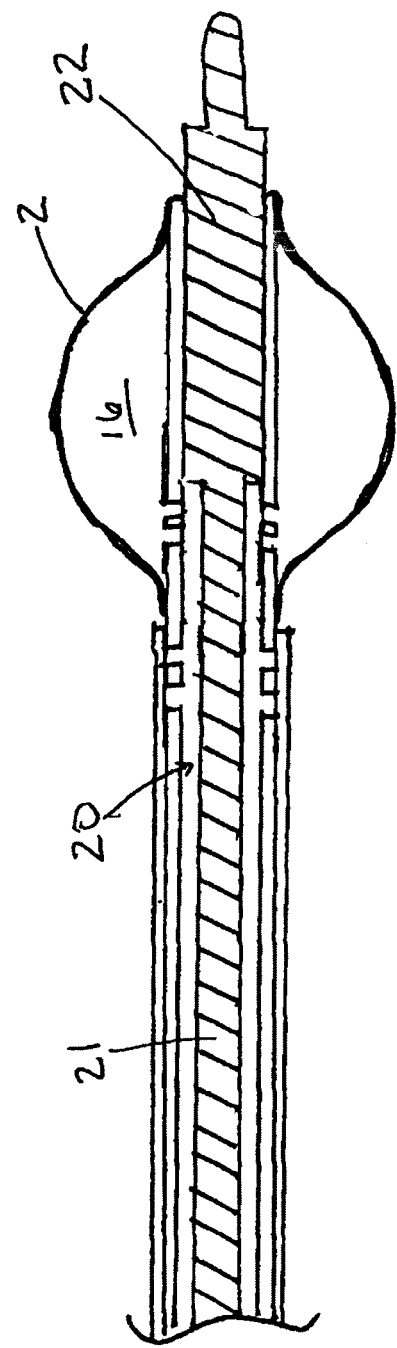

In order to control the flow of an inflation medium into and out of the cavity 16 of the expandable structure 2 an elongate wire 20 is positioned within the lumen 10 of the elongate hollow shaft 5 at a time when the treatment catheter 1 is being delivered to the treatment site or at a time subsequent to the treatment catheter 1 is being delivered to the treatment site. In the latter case, the treatment catheter 1 may be guided to the treatment site by the use of a conventional guidewire. According to some implementations a majority of a proximal length 21 of the elongate wire 20, commencing at or near a proximal end thereof, has an outer diameter A less than the inner diameter B of the elongate hollow shaft 5. Such an arrangement permits a passage of an inflation medium (see FIGS. 2B and 4) and/or a treatment agent (see FIG. 5) through the elongate hollow shaft 5. In the implementation of FIGS. 2A and 2B the elongate wire 20 further includes a distal end segment 22 with an outer surface 25 that is in sliding engagement with the inner surface 8 of the elongate hollow shaft 5. In the implementation of FIGS. 2A and 2B the distal end segment 22 of the elongate wire 20 constitutes a seal unit that is adapted to occlude the flow of an inflation medium into the cavity 16 of the expandable structure 2 when the elongate wire 20 assumes a first axial position as depicted in FIG. 2A, and that is further adapted to permit the flow of an inflation medium into the cavity 16 of the expandable structure 2 when the elongate wire 20 assumes a second axial position as depicted in FIG. 2B. According to some implementations the outer surface 25 of the distal end segment 22 is coated with a hydrophilic coating to enhance the distal end segment's ability to slide along the inner surface 8 of the hollow shaft 5.

As shown in the figures, the distal end of the elongate wire 20 may comprise an end segment 29 that extends distally to the seal unit. According to some implementations the end segment comprises an atraumatic distal tip 29a. According to some implementations end segment 29 has a length sufficient for the treatment catheter 1 to be self-guided through at least a portion of the bodily duct.

Figure 3B:
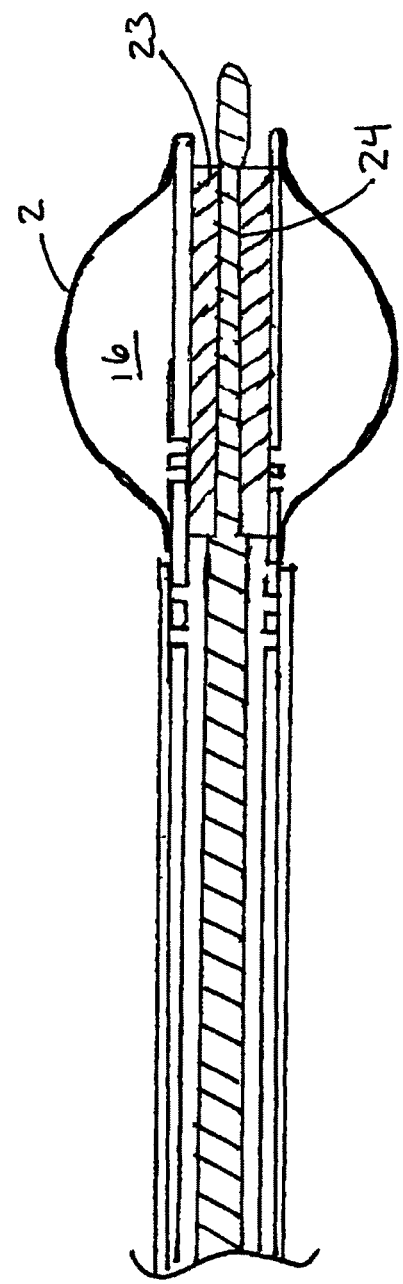

FIG. 3A illustrates an alternative implementation wherein the seal unit comprises an elastomeric material 23 positioned about the outer surface 24 of the elongate wire 20. The outer surface 24 may be surface treated (e.g. roughened, coated with an agent to produce a tacky surface, etc.) to enhance an adherence of the elastomeric material 23 to the elongate wire 20. Independently of or in conjunction with surface treating the outer surface 24 of the elongate wire 20, the elastomeric material 23 may at least partially reside within a recess of the elongate wire as shown in FIG. 3B. The elastomeric material may comprise any of a variety of medical grade materials such as, for example, silicone.

According to some implementations the elongate wire 20 comprises a hypotube with an internal lumen that extends distally from a proximal end to the distal end portion of the elongate wire. According to such implementations the seal unit may comprise an inflatable membrane (e.g. balloon-like structure) attached to the distal end portion of the elongate wire 20. To this end, the wall of the hypotube may comprise micro-channels for introducing an inflation medium into an internal cavity of the inflatable membrane to effectuate an inflation thereof. Prior to inflation, an inner wall of the membrane rests against an outer surface of the elongate wire 20. In use, the elongate wire according to such implementations may perform two functions. At a time prior to the membrane being inflated, the elongate wire 20 may be used as a conventional guidewire to assists in guiding the treatment catheter 1 through a bodily duct system of a patient to a treatment site. Upon the treatment catheter 1 being placed at the treatment site the membrane may be positioned inside the inner lumen 10 of the elongate hollow shaft 5 and subsequently inflated to perform the function of a seal unit as discussed above. According to some implementations the outer surface of the inflatable membrane is coated with a hydrophilic coating to enhance its ability to slide along the inner surface 8 of the hollow shaft 5. In the implementations of FIGS. 3A and 4-8 the distal portion of elongate wire 20 may have a substantially uniform diameter A ranging between 0.008 inches and 0.012 inches. As noted above, when the seal unit is integral with and forms a single piece with the elongate wire 20, the diameter of the seal unit portion of the elongate wire 20 is approximately equal to the inner diameter B of the inner lumen 10 of the elongate hollow shaft 5. In such a case, the remaining distal portion of the elongate wire 20 may have a substantially uniform or tapering diameter A ranging between 0.008 inches and 0.012 inches.

FIG. 4 shows a treatment catheter with the sleeve 18 located in its first axial position and the elongate wire located in its second axial position. With the sleeve 18 and elongate wire 20 positioned as such, an inflation medium may be delivered through the inner lumen 10 of the elongate hollow shaft 5 and into the cavity 16 of the expandable structure 2 through the one or more first through openings 11 as illustrated by the arrows in FIG. 4. FIG. 5 shows the treatment catheter 1 with the elongate wire 20 in its first axial position and the sleeve 18 in its second axial position. With the elongate wire 20 and sleeve 18 in these respective positions the expandable structure 2 is caused to remain in an inflated state and a treatment agent may be delivered through the inner lumen 10 of the elongate hollow shaft 5 into the lumen 31 of the bodily duct 30 through the one or more second through openings 12 as illustrated by the arrows in FIG. 5.

According to some implementations, as shown in each of FIGS. 4 and 5, the various components of the treatment catheter 1 may include strategically positioned radiopaque markers to assisted in visualizing the position of the various components in relation to one another under fluoroscopy. For example, one or more of the distal end of the sleeve 18, the distal end of the expandable structure 2 and the proximal and distal ends of the seal unit 22 may be provided with radiopaque markers 26.

Figure 6B:
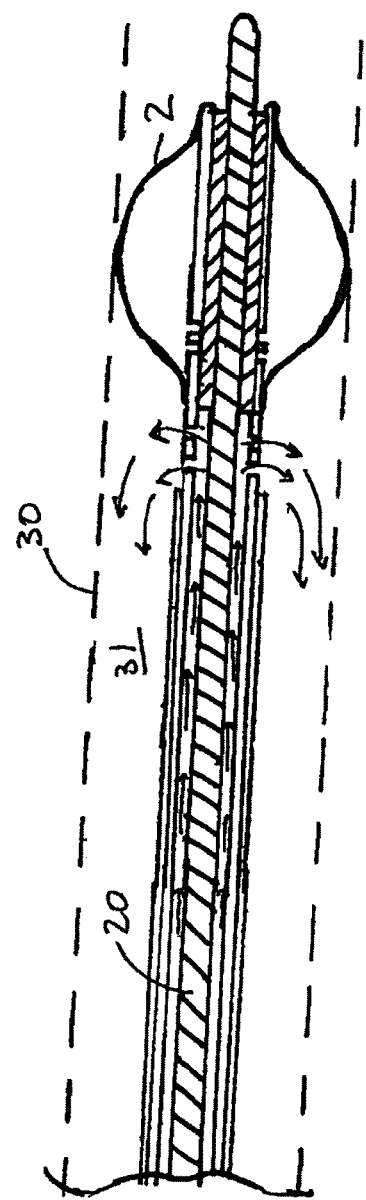

The catheter systems disclosed herein may be use for locally administering a treatment agent in a bodily duct of a patient. Treatments may include, but are not limited to, administering a drug to treat vasospasms, administering a drug to treat a diseased wall of the bodily duct, administering a drug or saline solution distally to an obstruction to effectuate a removal or fragmentation of the obstruction, etc. According to some implementations the treatment catheter 1 may be used alone to administer the treatment as shown in FIGS. 6A and 6B. According to other implementations, as will be discussed in more detail below with the respect to FIGS. 7 and 8, the treatment catheter 1 may be used in conjunction with an intermediate catheter 40.

A treatment method according to that depicted in FIGS. 6A and 6B involves a placement of the treatment catheter 1 in the bodily duct 30 so that the expandable structure 2 resides distal to the site to be treated. As discussed above, placement of the treatment catheter may occur with or without the elongate wire 20 being positioned within the lumen 10 of the elongate hollow shaft 5. In the latter case, the treatment catheter 1 may be guided to the treatment site by use of a conventional guidewire. In such instances, once the treatment catheter 1 is positioned at or near the treatment site, the convention guidewire may be removed from the treatment catheter. The elongate wire 20 may then been introduced into the lumen 10 of the elongate hollow shaft 5. In any event, at a point in time after the elongate wire 20 has been positioned within the elongate hollow shaft 5, it is positioned in the second axial position as depicted in FIG. 2B to permit the delivery of an inflation medium into the cavity 16 of the expandable structure 2. Subsequent to the expandable structure 2 being inflated to occlude flow through the bodily duct 30 as shown in FIG. 6A, the elongate wire 20 is moved to the second axial position to lock the inflation medium inside the cavity 16 of the expandable structure 2 to maintain the expandable structure 2 in the expanded state. A treatment agent may then be infused into the lumen 31 of the bodily duct 30 by moving the sleeve 18 from its first axial position to its second axial position and delivering the treatment agent through the inner lumen 10 of the elongate hollow shaft 5 and through the one or more second through holes 12 as shown in FIG. 6B.

Figure 9:
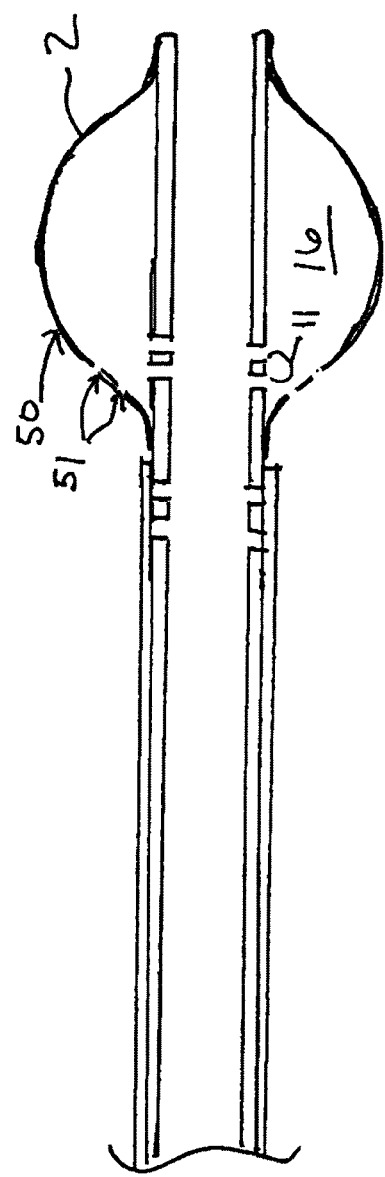

According to some implementations a proximal side 50 of the expandable structure 2 comprises a porous material that permits an elution of a fluid there through. According to other implementations, as shown in FIG. 9, one or more through holes 51 are provided in the proximal side 50 of the expandable structure 2 to permit an infusion of a treatment there through. According to each of these implementations a treatment agent may be delivered to the inner lumen 31 of the bodily duct 30 exclusively through the proximal side 50 of the expandable structure 2 or delivered concurrently though the expandable structure 2 and the one or more second through holes 12 in the elongate hollow shaft 5. In the latter case, each of the elongate wire 20 and sleeve 18 are positioned in their respective second axial positions during delivery of the treatment agent. When delivery of the treatment agent occurs exclusively through the expandable structure 2, the treatment catheter 1 may be devoid of the sleeve 18 and the one or more second through holes 12.

Figure 7B:
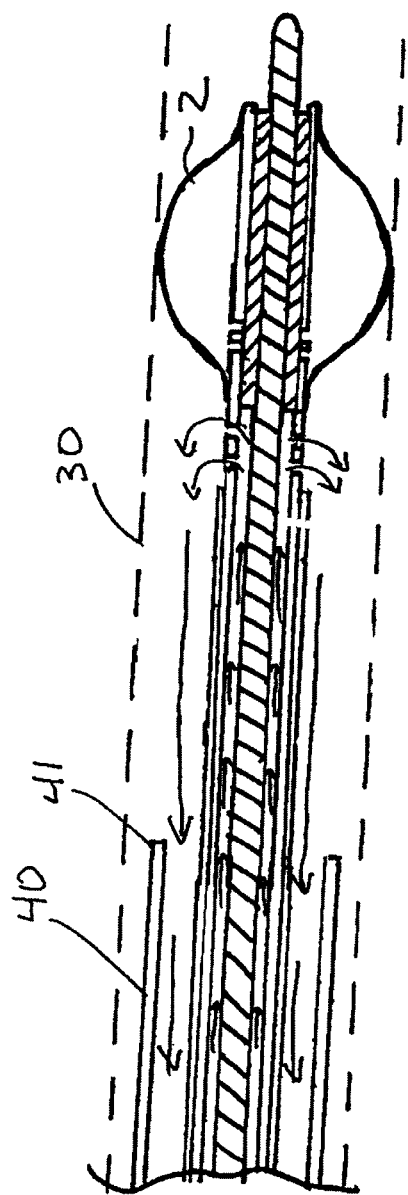

A treatment method according to that depicted in FIGS. 7A and 7B involves the use of a treatment catheter 1 and an intermediate catheter 40. According to some implementations the intermediate catheter 40 is an aspiration catheter as will be discussed in more detail below. Placement of the treatment catheter 1 in the bodily duct 30 may occur in at least two ways. According to a first method the treatment catheter 1 is situated inside the lumen 42 of the intermediate catheter 40 and delivered together to a location proximate the designated treatment site. In such a case, the distal end 41 of the intermediate catheter 40 and the expandable structure 2 of the treatment catheter 1 are caused to be spaced-apart with the treatment site residing between them. Separation may occur by advancing the treatment catheter 1 distal to the distal end 41 of the intermediate catheter or by retracting the intermediate catheter 40 proximally away from the expandable structure 2. According to a second method, the intermediate catheter 40 is first placed in the bodily duct 30 so that its distal end 41 is located in proximity to the treatment site. The treatment catheter 1 is then delivered to the treatment site through the lumen 41 of the intermediate catheter 40 so that the expandable structure 2 resides distal to the treatment site. As in the aforementioned case, the distal end 41 of the intermediate catheter 40 and the expandable structure 2 of the treatment catheter 1 are caused to be spaced-apart with the treatment site residing between them. As discussed above, placement of the treatment catheter may occur with or without the elongate wire 20 being positioned within the lumen 10 of the elongate hollow shaft 5. When the treatment catheter 1 is delivered to the treatment site without the elongate wire 20, the treatment catheter 1 may be guided to the treatment site by use of a conventional guidewire that is fed through the inner lumen 10 of the elongate hollow shaft 5. In such instances, once the treatment catheter 1 is positioned at or near the treatment site, the convention guidewire may be removed from the treatment catheter. The elongate wire 20 may then been introduced into the lumen 10 of the elongate hollow shaft 5. In any event, at a point in time after the elongate wire 20 has been positioned within the elongate hollow shaft 5, it is positioned in the second axial position as depicted in FIG. 2B to permit the delivery of an inflation medium into the cavity 16 of the expandable structure 2. Subsequent to the expandable structure 2 being inflated to occlude flow through the bodily duct 30 as shown in FIG. 7A, the elongate wire 20 is moved to the second axial position to lock the inflation medium inside the cavity 16 of the expandable structure 2 to maintain the expandable structure 2 in the expanded state. A treatment agent may then be infused into the lumen 31 of the bodily duct 30 by moving the sleeve 18 from its first axial position to its second axial position and delivering the treatment agent through the inner lumen 10 of the elongate hollow shaft 5 and through the one or more second through holes 12 as shown in FIG. 7B.

Figure 7D:
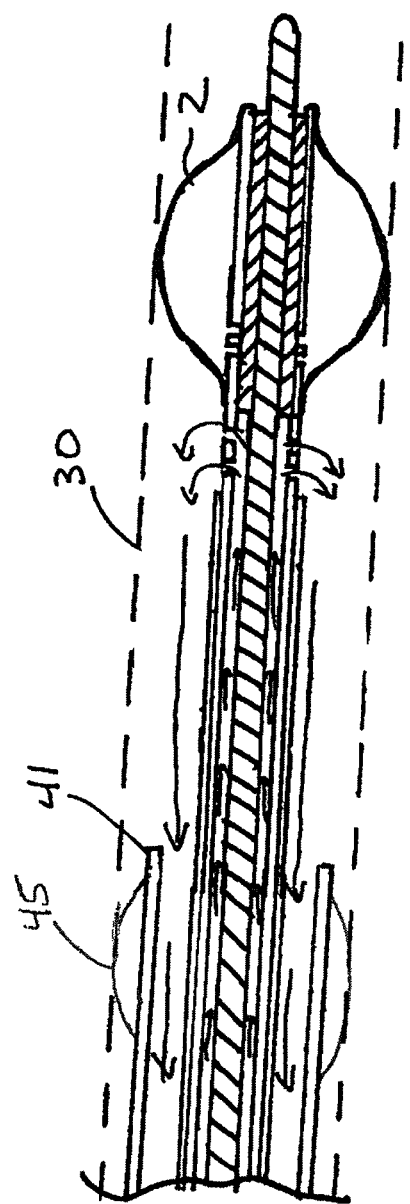

According to some implementations, the intermediate catheter 40 has a balloon 45 disposed on a distal section thereof. In some instances, as shown in FIGS. 7C and 7D, the balloon 45 is disposed near the distal end 41 of the intermediate catheter 40. During a delivery of the intermediate catheter to the treatment site the balloon 45 is typically in a deflated state and is thereafter inflated to inhibit a flow of the treatment agent proximal to the balloon. In this manner, according to some implementations, the treatment site is situated between the balloon 45 of the intermediate catheter 40 and the expandable structure 2. Although not shown in FIGS. 7C and 7D, the intermediate catheter 40 possess an inflation lumen to facilitate the delivery of an inflation medium to the interior of the balloon 45. According to other implementations a balloon guide catheter, not shown in the figures, may be used to assist in placing the treatment catheter 1 at the treatment site. In such implementations a balloon located near a distal end of the guide catheter may function much in the same way as balloon 45 described above to create a treatment zone that is situated between the balloon and the expandable structure 2 of the treatment catheter. The balloon guide catheter may be used with or without the involvement of an intermediate catheter 40.

With continued reference to FIG. 7B, according to some implementations the intermediate catheter 40 may also function as an aspiration catheter whereby a negative pressure may be established in the lumen 42 by applying a suction at a proximal end portion thereof. Use of the intermediate catheter 40 in this manner facilitates a local and yet non-systemic delivery of a treatment agent into the bodily duct 30 as a result of all or a majority of the treatment agent being removed through the intermediate catheter 40.

Figure 8B:
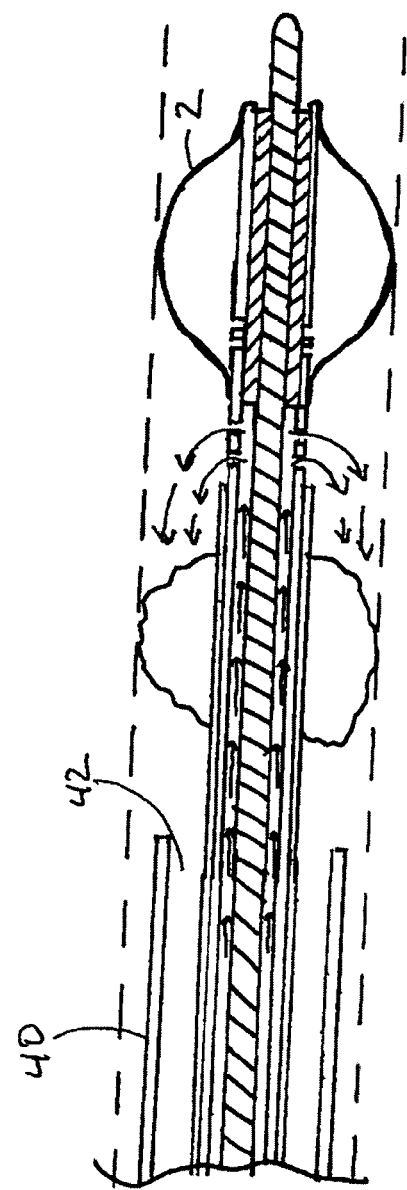
FIG. 8B shows the assembly of FIG. 8A wherein which a treatment agent is being infused into the bodily duct upstream the obstruction and aspirated proximal to the obstruction through an intermediate catheter.

FIGS. 8A and 8B show the treatment catheter 1 in use with the intermediate catheter 40 to effectuate at least a partial removal of an obstruction 60 that fully or partially occludes a portion of the bodily duct 30. The obstruction 60 may be, for example, a blood clot located in the vascular system of a patient. Placement of each of the intermediate catheter 40 and treatment catheter 1 may occur in a manner consistent with those described above in conjunction with FIG. 7. Once the treatment catheter 1 and intermediate catheter 40 have been placed in their respective positions within the bodily duct 30 as shown in FIG. 8A, a treatment agent may be introduced into the inner lumen 10 of the elongate hollow shaft 5 and the sleeve 18 moved to its second axial position to effectuate a flow of the treatment agent into the lumen 31 of the bodily duct 30 as shown in FIG. 8B. As with the previous implementations, the treatment agent is administered at a pressure sufficient to establish a retrograde flow as shown by the arrows in FIG. 8B. The treatment agent may be a drug that induces a fragmentation of the obstruction 60. When the obstruction 60 is a blood clot, the treatment agent may be, for example, a tissue plasma activation drug. According to other methods the treatment agent may simply be a saline solution, and in some instances may be the same saline solution used to inflate the expandable structure 2.

Figure 8C:
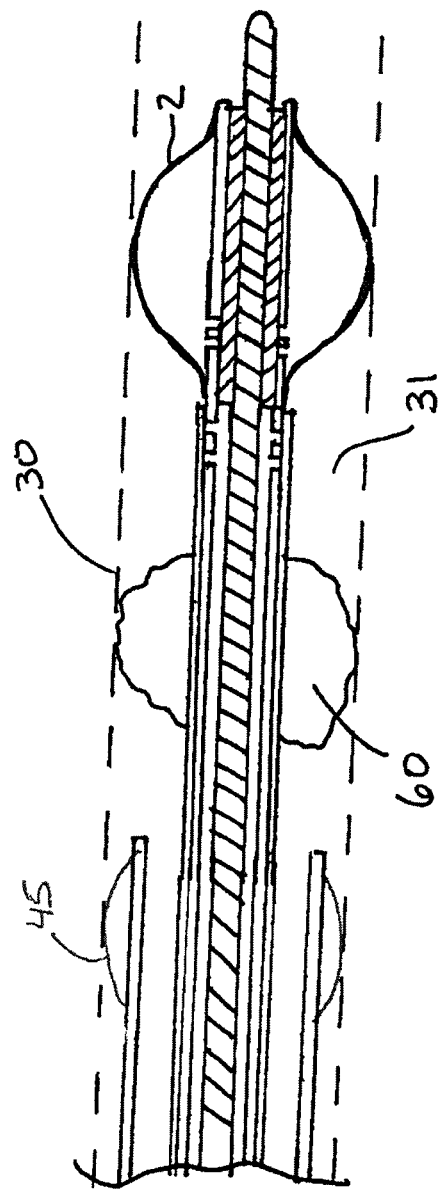
FIGS. 8C and 8D illustrate a treatment system similar to the system of FIGS. 8A and 8B with the intermediate catheter having a balloon disposed on a distal section thereof.
Figure 8D:
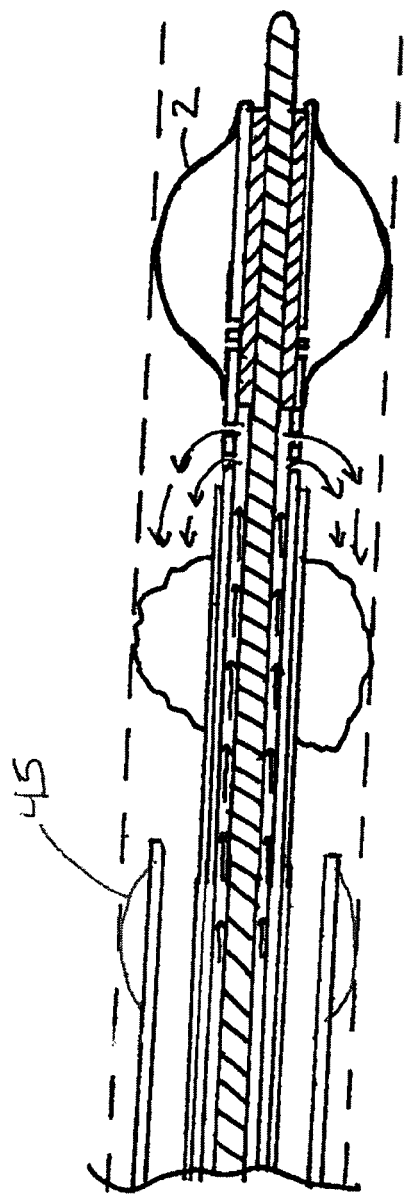

According to some implementations, the intermediate catheter 40 has a balloon 45 disposed on a distal section thereof. In some instances, as shown in FIGS. 8C and 8D, the balloon 45 is disposed near the distal end 41 of the intermediate catheter 40. During a delivery of the intermediate catheter to the treatment site the balloon 45 is typically in a deflated state and is thereafter inflated to inhibit a flow of the treatment agent proximal to the balloon. In this manner, according to some implementations, the obstruction 60 is situated between the balloon 45 of the intermediate catheter 40 and the expandable structure 2. Although not shown in FIGS. 8C and 8D, the intermediate catheter 40 possess an inflation lumen to facilitate the delivery of an inflation medium to the interior of the balloon 45. According to other implementations a balloon guide catheter, not shown in the figures, may be used to assist in placing the treatment catheter 1 at the treatment site proximal to the obstruction 60. In such implementations a balloon located near a distal end of the guide catheter may function much in the same way as balloon 45 described above to isolate the obstruction 60 between the balloon and the expandable structure 2 of the treatment catheter. The balloon guide catheter may be used with or without the involvement of an intermediate catheter 40.

According to implementations that involve the use of an intermediate catheter 40, the ratio of the inner diameter D of the intermediate catheter lumen 42 to the outer diameter C of the elongate hollow shaft 5 (the ratio D/C) may be between 1.5 and 5.0, and preferably between 2.0 and 4.0.

Although not shown in the figures, one or more of the elongate hollow shaft 5, sleeve 18 and elongate wire 20 may comprises one or more stop elements for limiting movement between the respective parts. For example, according to some implementations stops are provided to limit the movement of the sleeve 18 between its first and second axial positions. Further, one or more stops may be provided to limit the distal advancement of the elongate wire 20 to a position as shown, for example, in FIG. 2B. According to some implementations one or more stops are further provided to limit the proximal movement of the elongate wire 20 to a position as shown, for example, in FIG. 2A.

Upon the completion of a treatment procedure it is necessary to at least partially deflate the expandable structure 2 in order to facilitate a removal of the treatment catheter 1 from the patient. One method is to position the elongate wire 20 in its second axial position to permit a flow of the inflation medium into the inner lumen 10 of the elongate hollow shaft 5. In some instances a suction is applied to a proximal end of the lumen 10 to assist in extracting the inflation medium from the cavity 16 of the expandable structure 2. According to other implementations deflation is facilitated by placing each of the sleeve 18 and the elongate wire 2 in its respective second axial position to establish an inflation medium flow path between the cavity 16 and the lumen 31 of the bodily duct 30. According to other implementations the elongate wire 20 may be advanced a distance distally to establish a flow path between the cavity 16 and the lumen 31 of the bodily duct 30 through a distal end of the elongate hollow shaft 5.

According to anyone of the methods disclosed herein, the expandable member (e.g. balloon) may also provide protection from emboli travelling distal to the treatment site when it is in the expanded state. The expandable structure may also be used in the removal of an obstruction by withdrawing the expandable structure proximally after it has assumed its expanded state to assist in dislodging the obstruction. Further, at any given time during the removal of an obstruction a contrast medium may be infused through the one or more second through openings 12 to assist in visualizing the removal of the obstruction.

Figure 11:
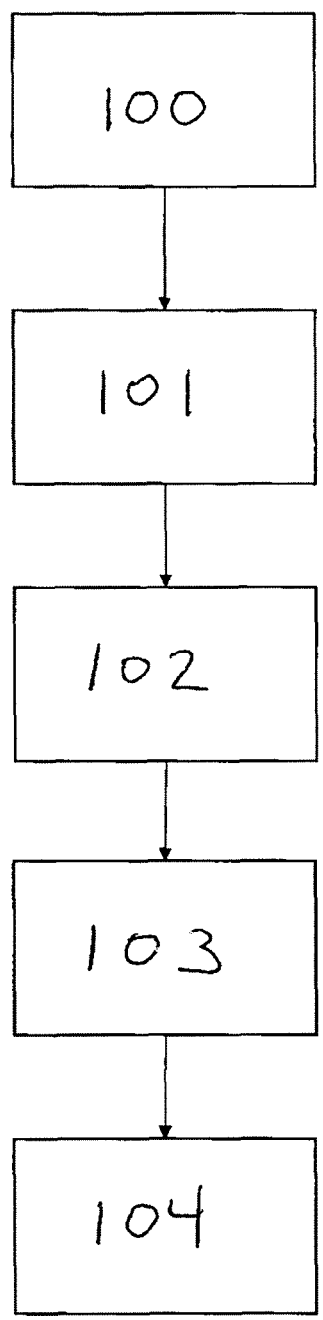
FIG. 11 is a flow chart of a method of administering a treatment agent to a treatment site in the bodily duct of a patient according to one implementation.

FIG. 11 is a flow diagram of a method of administering a treatment agent to a treatment site in the bodily duct 30 of a patient. At step 100 the treatment catheter is positioned within the lumen 31 of the bodily duct 30 so that the entirety of the expandable structure 2 resides distal to the treatment site. At step 101, if the elongate wire 20 is not already in its second axial position, the elongate wire is moved to its second axial position. At step 102 an inflation medium is introduced into a proximal end of the inner lumen 10 of the elongate hollow shaft 5 at a pressure sufficient to cause the inflation medium to flow though the first one or more through holes 11 of the elongate hollow shaft 5 to cause the expandable structure 2 to assume the expanded configuration. At step 103, with the expandable structure being in the expanded configuration the sleeve is moved from its first axial position to its second axial position. At step the treatment agent is introduced into the proximal end of the inner lumen 10 of the elongate hollow shaft 5 at a pressure sufficient to cause the treatment agent to flow through the second one or more holes 12 of the elongate hollow shaft 5 and into the lumen 31 of the bodily duct 30.

Figure 12:
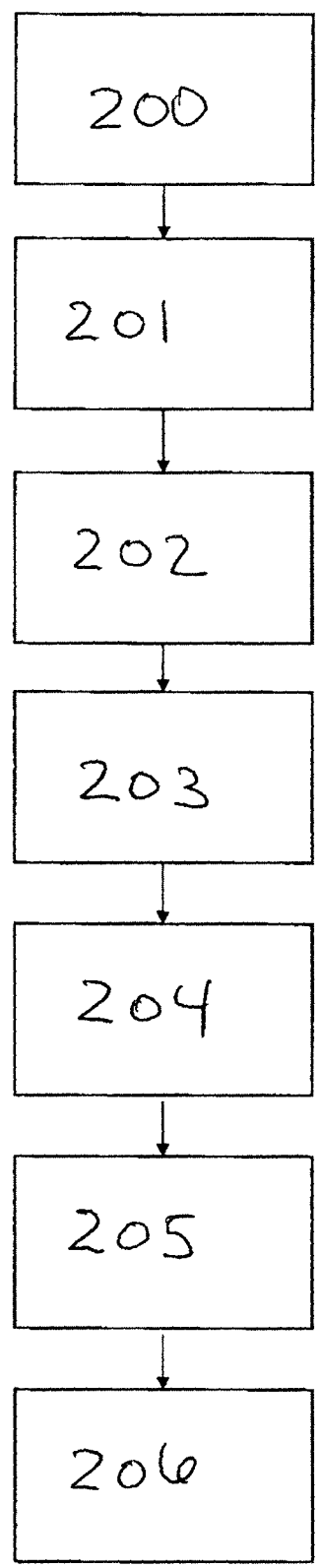
FIG. 12 is a flow chart of a method for removing an obstruction in a bodily duct of a patient according to one implementation.

FIG. 12 is a flow diagram of a method for removing an obstruction 60 in a bodily duct 30 of a patient. At step 200 an intermediate catheter 40 is obtained that includes an elongate lumen 42 that is open at a distal end 41 thereof. At step 201 the intermediate catheter 40 is introduced into the bodily duct of the patient so that the open distal end 41 of the elongate lumen 42 is positioned near and proximal to the obstruction 60. At step 202 the treatment catheter is advanced through the elongate lumen 42 of the intermediate catheter 40 and into the bodily duct 30 so that the entirety of the expandable structure 2 resides distal to the obstruction 60. At step 203 if the elongate wire 20 is not already in its second axial position, the elongate wire 20 is moved to its second axial position. At step 204 an inflation medium is introduced into a proximal end of the inner lumen 10 of the elongate hollow shaft 5 at a pressure sufficient to cause the inflation medium to flow though the first one or more holes 11 of the elongate hollow shaft 5 to cause the expandable structure 2 to assume the expanded configuration. At step 205, with the expandable structure 2 being in the expanded configuration, moving the sleeve 18 from its first axial position to its second axial position. At step 206 a treatment agent is introduced into the proximal end of the inner lumen 10 of the elongate hollow shaft 5 at a pressure sufficient to cause the treatment agent to flow through the second one or more holes 12 of the elongate hollow shaft 5 and into the bodily duct 30. At step 207 at least a portion of the treatment agent is aspirated through the elongate lumen 42 of the intermediate catheter 40.

Figure 15A:
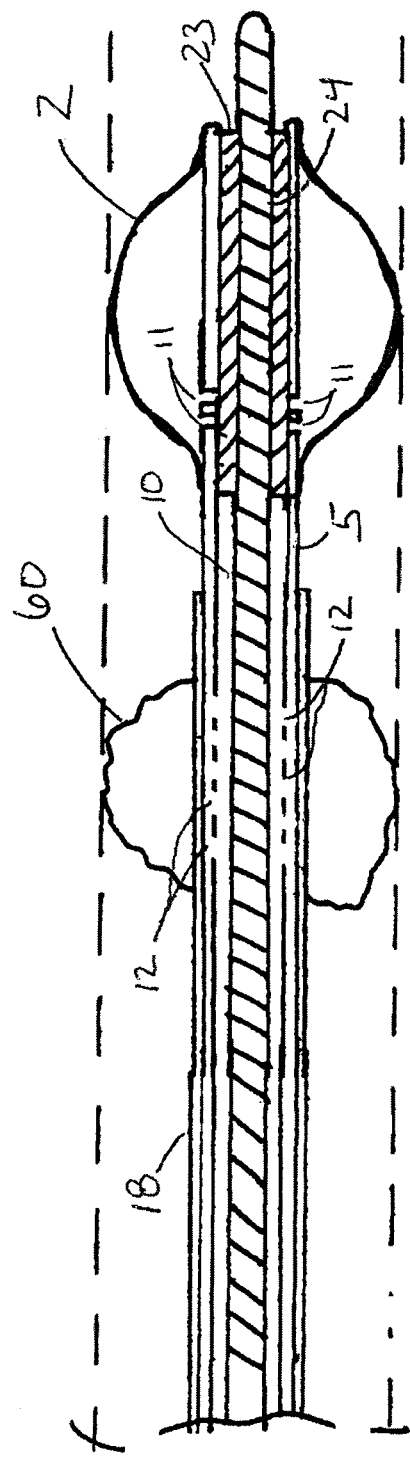
Figure 16:
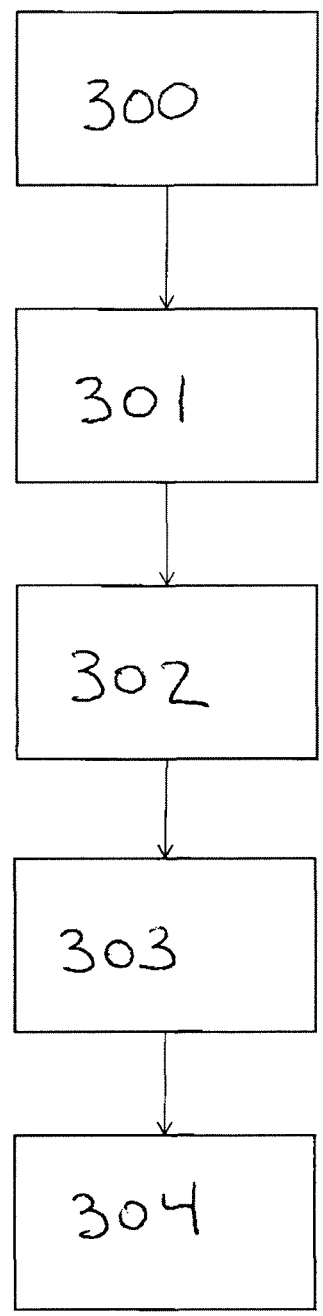
FIG. 16 is a flow chart of a method for removing an obstruction in a bodily duct of a patient according to one implementation.

FIGS. 15A and 15B illustrate an assembly for removing an obstruction 60 from the bodily duct 30 of a patient according to another implementation. The assembly includes a treatment catheter 1 similar to that disclosed above that is used to at least partially remove the obstruction 60 through the second one or more through openings 12 by applying a suction pressure at a proximal end of the treatment catheter. FIG. 16 is a flow diagram of a method for removing the obstruction 60 by use of said assembly. At step 300 the treatment catheter 1 is placed at the treatment site so that the expandable member 2 resides downstream the obstruction 60 and so that the second one or more through openings 12 reside in an interior of the obstruction. At step 301 the expandable member 2 is caused to expand according to any one of the methods previously described herein. At step 302, the sleeve 18 is retracted proximally to in order to communicate the inner lumen 10 of the elongate hollow shaft 5 with the interior of the obstruction 60 via the second one or more through openings 12. At step 303, which may occur before or after step 302, a suction pressure is applied at a proximal end of the elongate hollow shaft 5 sufficient to effectuate at least a partial removal of the obstruction 60 from the lumen 31 of the bodily duct 30. According to some implementations, upon there being at least a partial removal of the obstruction 60 from the vessel 30, a further step 304 is employed that involves proximally retracting the treatment catheter 1 so that the expandable structure 2 engages with the obstruction 60 to push it proximally into an intermediate catheter 40, as described above, or to another proximal location where the obstruction may be removed from the lumen 31 of the bodily duct 30.

Figure 13B:
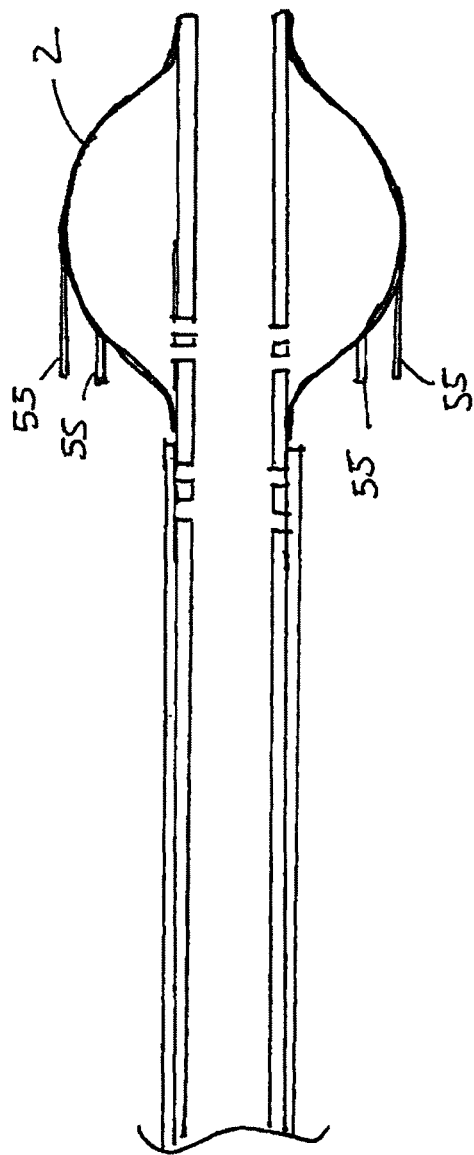

As noted above, the expandable structure 2 (e.g. balloon) may be used in the removal of an obstruction by withdrawing the expandable structure proximally after it has assumed its expanded state. A problem associated with the removal of blood clots, or other bodily duct obstructions, when using a balloon or cage-like structure is that the obstruction tends to roll along an outer surface of the balloon or cage as the balloon or cage is moved proximally in an attempt to dislodge the obstruction. According to some implementations, as shown in FIGS. 13A and 13B, the outer surface of the expandable structure 2 has attached thereto a plurality of proximally extending members 55 that assist in anchoring the obstruction to the expandable structure 2 when the expandable structure is moved proximally to engage with the obstruction. That is, as the expandable member 2 is advanced in a proximal direction to engage the obstruction 60, the proximally extending members 55 are adapted (possess sufficient stiffness) to pierce through at least a portion of the obstruction 60. By entrapping the obstruction between themselves and the leading outer surface of the expandable member 2, the proximally extending members 55 minimize the likelihood of the obstruction rolling over the expandable member 2 as it is advanced proximally against the distal side of the obstruction. FIGS. 13A and 13B show the use of 2 and 4 proximally extending members 55, respectively. It is appreciated, however, that any number of proximally extending members 55 may be employed. According to some implementations the proximally extending members are spaced equidistantly about the circumference of the expandable member 2. The proximally extending members 55 may comprise any of a variety of medical grade materials, including, but not limited to, metals (e.g. nitinol) and low elasticity polymers (e.g. Pebax).

Figure 13C:
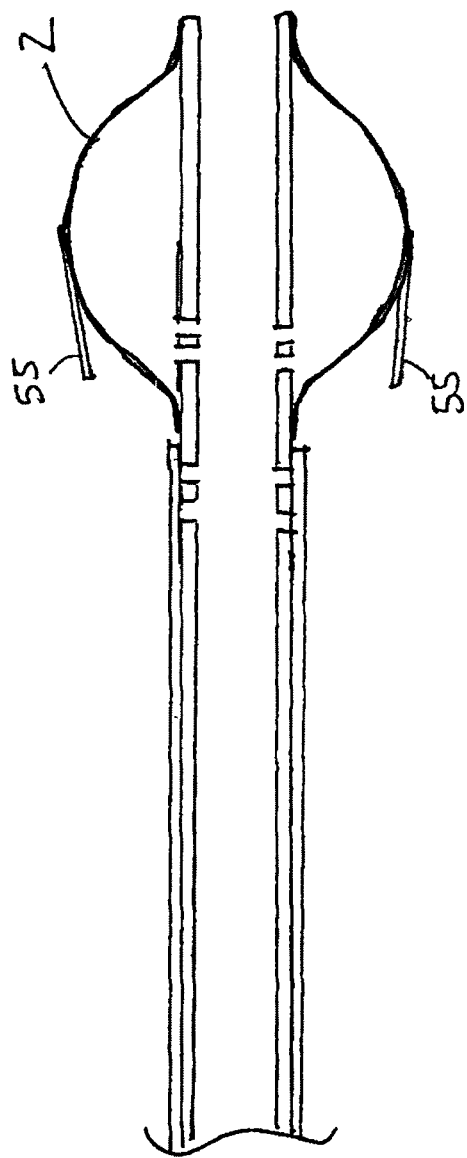

According to some implementations, as shown in FIG. 13C. all or at least some of the proximally extending members 55 are oriented on the expandable structure 2 in a manner so that they incline downward toward the center of the catheter when the expandable structure 2 assumes its expanded configuration. The downward inclination reduces the risk of the proximally extending members 55 adversely interfering with or piercing the luminal wall of the vessel under treatment.

According to some implementations, at least the leading outer surface 56 of the expandable structure 2 may alternatively, or in conjunction with the use of the proximally extending members 55, be surface treated or coated with a compound to increase its surface roughness.

Figure 14A:
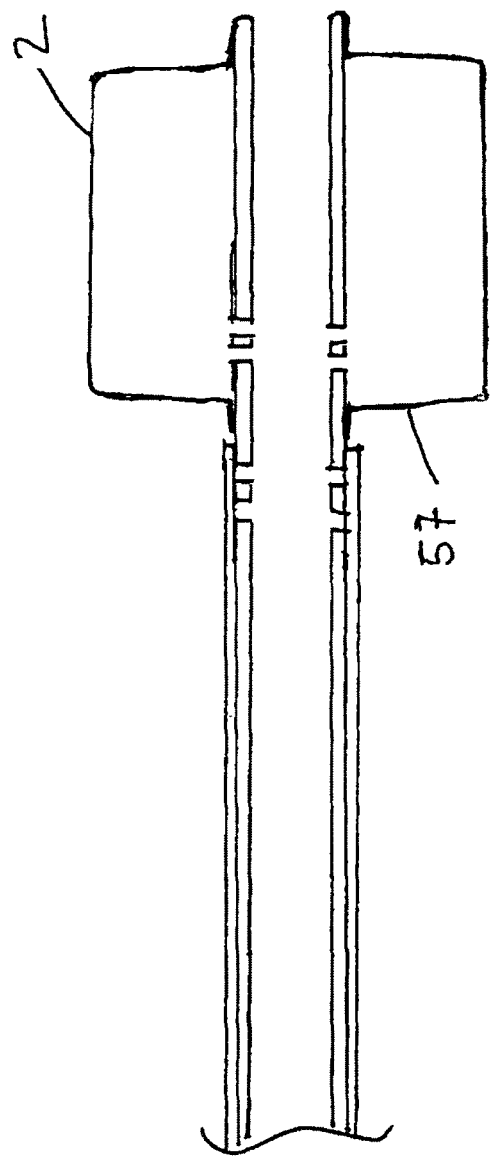
FIG. 14A illustrates a catheter with a blunt face balloon according to one implementation.
Figure 14B:
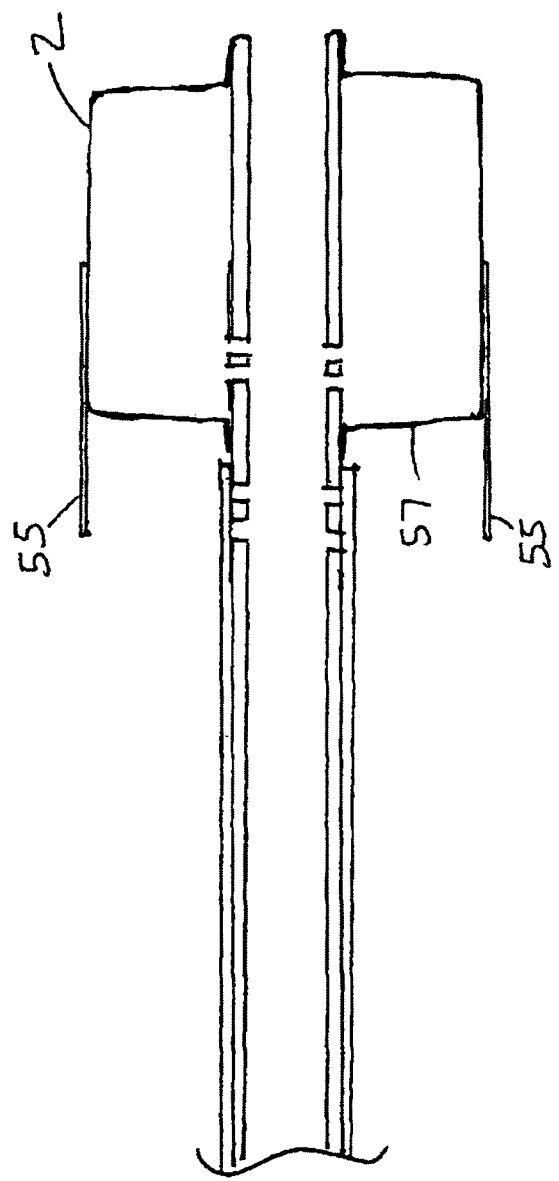
FIG. 14B illustrates the balloon of FIG. 14A having proximally extending members.

According to some implementations, as shown in FIG. 14A, the expandable member 2 is a balloon constructed to have a blunt leading face 57 versus a sloping curvilinear face illustrated in the previous implementations. The blunt leading face 57 may be substantially vertical or may have an angle of inclination of less than 10 degrees, and preferably of less than 5 degrees. The blunt face feature may be incorporated into any of the implementations disclosed or contemplated herein. A particular advantage of the blunt leading face 57 is that it is less accommodating in permitting the obstruction 60 to roll over the outer surface of the balloon 2 when the balloon is being used to remove the obstruction. Like the implementations of FIGS. 13A and 13B, the blunt face balloon of FIG. 14A may further comprise proximally extending members 55 as shown in FIG. 14B to assist in anchoring the obstruction 60 to the balloon 2 when it is being used to remove the obstruction. At least the blunt face 57 of the balloon 2 may also be surface treated or coated with a compound to increase its surface roughness.

The particular features, structures or characteristics of any implementation described above may be combined in any suitable manner, as would be apparent to one of ordinary skill in the art from this disclosure, in one or more implementations. Similarly, it should be appreciated that in the above description of implementations, various features of the inventions are sometimes grouped together in a single implementation, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed implementations. The claims following the Detailed Description are hereby expressly incorporated into this Detailed Description, with each claim standing on its own as a separate implementation.

What is claimed is:

1. A treatment catheter for placement in a bodily duct of a patient, the treatment catheter comprising:
    an expandable structure,
    an elongate hollow shaft having a wall with a first through hole and a second through hole, the first through hole spaced axially apart from the second through hole, the elongate hollow shaft having a proximal end portion and a distal end portion, the expandable structure being disposed about the distal end portion of the elongate hollow shaft such that the first through hole resides beneath the expandable structure, the second through hole being located proximal to the expandable structure,
    a sleeve positioned along an outer surface of the elongate hollow shaft moveable between first and second axial positions to respectively permit and inhibit the flow of a treatment agent through the second through hole into the bodily duct,
    an elongate wire having a seal unit positioned within an inner lumen of the elongate hollow shaft, the seal unit positioned at least partially beneath the expandable structure and being moveable between first and second axial positions to respectively permit and inhibit the flow of an inflation medium between a cavity of the expandable structure and the inner lumen of the hollow shaft through the first through hole, the first axial position being located distal to the second axial position.

2. The treatment catheter according to claim 1, wherein a cross-sectional area of the elongate wire located proximal to the seal unit is less than a cross-sectional area of the inner lumen of the elongate hollow shaft.

3. The treatment catheter according to claim 1, wherein the elongate hollow shaft is made of a metal.

4. The treatment catheter of claim 3, wherein the proximal end portion of the elongate hollow shaft comprises a hypotube.

5. The treatment catheter according to claim 3, wherein the elongate hollow shaft has an outer diameter of between 0.025 inches and 0.035 inches.

6. The treatment catheter according to claim 4, wherein the elongate hollow shaft has an outer diameter of between 0.025 inches and 0.035 inches.

7. The treatment catheter according to claim 6, wherein the wall of the elongate hollow shaft has a thickness between 0.004 inches and 0.006 inches.

8. The treatment catheter according to claim 5, wherein the distal portion of the elongate hollow shaft comprises a plurality of cuts extending into the outer surface to enhance the flexibility of the distal portion.

9. The treatment catheter according to claim 1, wherein a compression fit exists between an outer surface of the seal unit and an inner surface of the elongate hollow shaft.

10. The treatment catheter according to claim 1, wherein a compression fit exists between the sleeve and the outer surface of the elongate hollow shaft.

11. The treatment catheter according to claim 1, wherein the seal unit comprises an elastomer material disposed along a length of an outer surface of the elongate wire.

12. The treatment catheter according to claim 11, wherein the elastomer material resides within a recess in the outer surface of the elongate wire.

13. The treatment catheter according to claim 11, wherein the outer surface of the elongate wire is roughened to enhance an adhesion of the elastomer to the elongate wire.

14. The treatment catheter according to claim 11, wherein the elastomer material is silicone.

15. The treatment catheter according to claim 1, wherein the seal unit comprises a proximal end and a distal end and the elongate wire is provided with a first radiopaque marker adjacent the proximal end of the seal unit and with a second radiopaque marker adjacent the distal end of the seal unit.

16. The treatment catheter according to claim 1, wherein a distal end of the sleeve is provided with a third radiopaque marker.

17. The treatment catheter according to claim 15, wherein a distal end of the sleeve is provided with a third radiopaque marker.

18. The treatment catheter according to claim 17, wherein the distal end of the expandable structure is provided with a fourth radiopaque marker.

19. The treatment catheter according to claim 1, wherein one or more of the elongate wire, seal unit and distal end of elongate hollow shaft is provided with stop elements to delimit the axial movement of the seal unit between the first and second axial positions.

20. The treatment catheter according to claim 1, wherein the elongate wire comprises an end segment that extends distally to the seal unit, the end segment having a length sufficient for the treatment catheter to be self-guided through at least a portion of the bodily duct.

21. The treatment catheter according to claim 1, wherein the expandable structure is a balloon that comprises an inflatable membrane.

22. The treatment catheter according to claim 21, wherein the balloon has a length of between 2 to 10 millimeters.

23. The treatment catheter according to claim 21, wherein at least a portion of the expandable membrane located along the proximal portion of the balloon is porous.

24. The treatment catheter according to claim 21, wherein at least a portion of the expandable membrane located along the proximal portion of the balloon has one or more through openings.

25. The treatment catheter according to claim 1, wherein the expandable structure is an expandable cage with a cover disposed over an external surface of the expandable cage, the cover being made of a material capable of occluding the passage of a fluid there through.

26. The treatment catheter according to claim 25, wherein the expandable cage comprises a proximal portion and a distal portion, at least a portion of the cover overlying the proximal portion is porous.

27. The treatment catheter according to claim 25, wherein the expandable cage comprises a proximal portion and a distal portion, at least a portion of the cover overlying the proximal portion has one or more through openings.

\* \* \* \* \*